United States Patent
Andersen et al.

(10) Patent No.: US 6,280,995 B1
(45) Date of Patent: Aug. 28, 2001

(54) PECTATE LYASES

(75) Inventors: Lene Nonboe Andersen, Allerød; Martin Schülein, Copenhagen, both of (DK); Niels Erik Krebs Lange, Raleigh, NC (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/546,500

(22) Filed: Apr. 11, 2000

Related U.S. Application Data

(62) Division of application No. 09/073,684, filed on May 6, 1998, now Pat. No. 6,124,127
(60) Provisional application No. 60/067,240, filed on Dec. 2, 1997.

(30) Foreign Application Priority Data

Nov. 24, 1997 (DK) .................................. 1344/97

(51) Int. Cl.⁷ ............................... C12N 9/88; C12N 1/20; C07H 21/04

(52) U.S. Cl. ..................... 435/232; 435/183; 435/252.3; 435/252.31; 435/252.33; 435/320.1; 536/23.2; 536/23.7

(58) Field of Search ..................................... 435/232, 183, 435/252.3, 252.33, 320.1, 252.31; 536/23.2, 23.7

(56) References Cited

PUBLICATIONS

Kim et al., (1994) Biosci. Biotech. Biochem. 58(5):947–949.
Nasser et al., (1993) FEBS 335(3):319–326.

*Primary Examiner*—Nashaat T. Nashed
(74) *Attorney, Agent, or Firm*—Elias Lambiris Esq.

(57) ABSTRACT

The present invention relate to microbial pectate lyase, more specifically to microbial enzyme exhibiting pectate lyase activity as their major enzymatic activity in neutral and alkaline pH ranges, to a method of producing such an enzyme, and a method for using such enzymes in the textile, detergent, and cellulose fiber processing industries.

5 Claims, No Drawings

PECTATE LYASES

CROSS-REFERENCE TO RELATED APPLICATIONS

This application is a divisional of U.S. application Ser. No. 09/073,684 filed May 6, 1998, now U.S. Pat. No. 6,124,127 and claims priority under 35 U.S.C. 119 of Danish application 1344/97 filed Nov. 24, 1997 and of U.S. Provisional application No. 60/067,240 filed Dec. 2, 1997, the contents of which are fully incorporated herein by reference.

The present invention relates to microbial pectate lyases, more specifically to microbial enzymes exhibiting pectate lyase activity as their major enzymatic activity in the neutral and alkaline pH ranges; to a method of producing such enzymes; and to methods for using such enzymes in the textile, detergent and cellulose fiber processing industries.

BACKGROUND OF THE INVENTION

Pectin polymers are important constituents of plant cell walls. Pectin is a hetero-polysaccharide with a backbone composed of alternating homogalacturonan (smooth regions) and rhamnogalacturonan (hairy regions). The smooth regions are inear polymers of 1,4-linked alpha-D-galacturonic acid. The galacturonic acid residues can be methyl-esterified on the carboxyl group to a varying degree, usually in a non-random fashion with blocks of polygalacturonic acid being completely methyl-esterified.

Pectinases can be classified according to their preferential substrate, highly methyl-esterified pectin or low methyl-esterified pectin and polygalacturonic acid (pectate), and their reaction mechanism, beta-elimination or hydrolysis. Pectinases can be mainly endo-acting, cutting the polymer at random sites within the chain to give a mixture of oligomers, or they may be exo-acting, attacking from one end of the polymer and producing monomers or dimers. Several pectinase activities acting on the smooth regions of pectin are included in the classification of enzymes provided by the Enzyme Nomenclature (1992) such as pectate lyasd (EC 4.2.2.2), pectin lyase (EC 4.2.2.10), polygalacturonase (EC 3.2.1.15), exo-polygalacturonase (EC 3.2.1.67), exo-polygalacturonate lyase (EC 4.2.2.9) and exo-poly-alpha-galacturonosidase (EC 3.2.1.82).

Pectate lyases have been cloned from different bacterial genera such as Erwinia, Pseudomonas, Klebsiella and Xanthomonas. Also from *Bacillus subtilis* (Nasser et al. (1993) FEBS 335:319–326) and Bacillus sp. YA-14 (Kim et al. (1994) *Biosci. Biotech. Biochem.* 58:947–949) cloning of a pectate lyase has been described. Purification of pectate lyases with maximum activity in the pH range of 8–10 produced by *Bacillus pumilus* (Dave and Vaughn (1971) J. Bacteriol. 108:166–174), *B. polymyxa* (Nagel and Vaughn (1961) Arch. Biochem. Biophys. 93:344–352), *B. stearothermophilus* (Karbassi and Vaughn (1980) Can. J. Microbiol. 26:377–384), Bacillus sp. (Hasegawa and Nagel (1966) J. Food Sci. 31:838–845) and Bacillus sp. RK9 (Kelly and Fogarty (1978) Can. J. Microbiol. 24:1164–1172) has been reported, however, no publication was found on cloning of pectate lyase encoding genes from these organisms. All the pectate lyases described require divalent cations for maximum activity, calcium ions being the most stimulatory.

Generally, pectinase producing microorganisms exhibit a broad range of pectin degrading or modifying enzymes. Often the microorganisms also produce cellulases and/or hemicellulases and complex multi-component enzyme preparations from such microorganisms may be difficult to optimise for various applications, they even may contain enzymes with detrimental effect. Thus, it is an object of the present invention to provide a pectin degrading enzyme exhibiting only the desired effects e.g. in detergents or different industrial processes.

SUMMARY OF THE INVENTION

The inventors have now found a novel enzyme having substantial pectate lyase activity, i.e. an enzyme exhibiting pectate lyase activity which may be obtained from a bacterial strain of the genus Bacillus, more specifically of the strain *Bacillus licheniformis*, and have succeeded in identifying a DNA sequence encoding such enzyme. The DNA sequence and the deduced amino acid sequence are listed in the sequence listing as SEQ ID No. 1 and 2, respectively. It is believed that the novel enzyme will be classified according to the Enzyme Nomenclature in the Enzyme Class EC 4.2.2.2. However, it should be noted that the enzyme of the invention also exhibits catalytic activity on pectin (which may be esterified) besides the activity on pectate and polygalacturonides conventionally attributed to enzymes belonging to EC 4.2.2.2.

In a first aspect, the present invention relates to a pectate lyase which is i) a polypeptide produced by *Bacillus licheniformis*, ATCC 14580, or ii) a polypeptide comprising an amino acid sequence as shown in positions 1–341 of SEQ ID NO:2, or iii) an analogue of the polypeptide defined in i) or ii) which is at least 70% homologous with said polypeptide, is derived from said polypeptide by substitution, deletion or addition of one or several amino acids, or is immunologically reactive with a polyclonal antibody raised against said polypeptide in purified form.

Within one aspect, the present invention provides an isolated polynucleotide molecule selected from the group consisting of (a) polynucleotide molecules encoding a polypeptide having pectate lyase activity and comprising a sequence of nucleotides as shown in SEQ ID NO: 1 from nucleotide 1 to nucleotide 1026; (b) species homologs of (a); (c) polynucleotide molecules that encode a polypeptide having pectate lyase activity that is at least 70% identical to the amino acid sequence of SEQ ID NO: 2 from amino acid residue 1 to amino acid residue 341; (d) molecules complementary to (a), (b) or (c); and (e) degenerate nucleotide sequences of (a), (b), (c) or (d).

The plasmid pSJ1678 comprising the polynucleotide molecule (the DNA sequence) encoding a pectate lyase of the present invention has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Sep. 25, 1997 under the deposition number DSM 11789.

Within another aspect of the invention there is provided an expression vector comprising the following operably linked elements: a transcription promoter; a DNA segment selected from the group consisting of (a) polynucleotide molecules encoding a polypeptide having pectate lyase activity and comprising a sequence of nucleotides as shown in SEQ ID NO: 1 from nucleotide 1 to nucleotide 1026; (b) species homologs of (a); (c) polynucleotide molecules that encode a polypeptide having pectate lyase activity that is at least 80% identical to the amino acid sequence of SEQ ID NO: 2 from amino acid residue 1 to amino acid residue 341; and (d) degenerate nucleotide sequences of (a), (b), or (c); and a transcription terminator.

Within yet another aspect of the present invention there is provided a cultured cell into which has been introduced an expression vector as disclosed above, wherein said cell expresses the polypeptide encoded by the DNA segment.

A further aspect of the present invention provides an isolated polypeptide having pectate lyase activity selected from the group consisting of (a) polypeptide molecules comprising a sequence of amino acid residues as shown in SEQ ID NO:2 from amino acid residue 1 to amino acid residue 399; (b) species homologs of (a).

Within another aspect of the present invention there is provided a composition comprising a purified polypeptide according to the invention in combination with other polypeptides.

Within another aspect of the present invention there are provided methods for producing a polypeptide according to the invention comprising culturing a cell into which has been introduced an expression vector as disclosed above, whereby said cell expresses a polypeptide encoded by the DNA segment and recovering the polypeptide.

The novel enzyme of the present invention is useful for the treatment of cellulosic material, especially cellulose-containing fiber, yarn, woven or non-woven fabric, treatment of mechanical paper-making pulps or recycled waste paper, and for retting of fibres. The treatment can be carried out during the processing of cellulosic material into a material ready for garment manufacture or fabric manufacture, e.g. in the desizing or scouring step; or during industrial or household laundering of such fabric or garment.

Accordingly, in further aspects the present invention relates to a detergent composition comprising an enzyme having substantial pectate lyase activity; and to use of the enzyme of the invention for the treatment of cellulose-containing fibers, yarn, woven or non-woven fabric.

The enzyme of the invention is very effective for use in an enzymatic scouring process in the preparation of cellulosic material e.g. for proper response in subsequent dyeing operations. Further, it is c ontemplated that detergent compositions comprising the novel enzyme are capable of removing or bleaching certain soils or stains present on laundry, especially soils and spots resulting from galactan or arabinogalactan containing food, plants, and the like. It is also contemplated that treatment with detergent compositions comprising the novel enzyme can prevent binding of certain soils to the cellulosic material.

DEFINITIONS

Prior to discussing this invention in further detail, the following terms will first be defined.

The term "ortholog" (or "species homolog") denotes a polypeptide or protein obtained from one species that has homology to an analogous polypeptide or protein from a different species.

The term "paralog" denotes a polypeptide or protein obtained from a given species that has homology to a distinct polypeptide or protein from that same species.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector it is to be introduced. Thus, the vector may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome and replicated together with th chromosome(s) into which it has been integrated.

The term "recombinant expressed" or "recombinantly expressed" used herein in connection with expression of a polypeptide or protein is defined according to the standard definition in the art. Recombinantly expression of a protein is generally performed by using an expression vector as described immediately above.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, Nature 316:774–78, 1985). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity (e.g. another polypeptide than the polypeptide of the invention) which originate from the homologous cell where the polypeptide of the invention is originally obtained from.

The term "obtained from" as used herein in connection with a specific microbial source, means that the polynucleotide and/or polypeptide produced by the specific source, or by a cell in which a gene from the source have been inserted.

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequende of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "pectin" denotes pectate, polygalacturonic acid, and pectin which may be esterified to a higher or lower degree.

The term "pectinase" denotes a pectinase enzyme defined according to the art where pectinases are a group of enzymes that cleave glycosidic linkages of pectic substances mainly poly(1,4-alpha-D-galacturonide and its derivatives (see reference Sakai et al., Pectin, pectinase and protopectinase: production, properties and applications, pp 213–294 in: Advances in Applied Microbiology vol:39,1993).

Preferably a pectinase of the invention is a pectinase enzyme which catalyzes the random cleavage of alpha-1,4-glycosidic linkages in pectic acid also called polygalacturonic acid by transelimination such as the enzyme class polygalacturonate lyase (EC 4.2.2.2) (PGL) also known as poly(1,4-alpha-D-galacturonide) lyase also known as pectate lyase.

DETAILED DESCRIPTION OF THE INVENTION

HOW TO USE A SEQUENCE OF THE INVENTION TO GET OTHER RELATED SEQUENCES:

The disclosed sequence information herein relating to a polynucleotide sequence encoding a pectate lyase of the invention can be used as a tool to identify other homologous pectate lyases. For instance, polymerase chain reaction (PCR) can be used to amplify sequences encoding other homologous pectate lyases from a variety of microbial sources, in particular of different Bacillus species.

ASSAY FOR ACTIVITY TEST

A polypeptide of the invention having pectate lyase activity may be tested for pectate lyase activity according to standard test procedures known in the art, such as by applying a solution to be tested to 4 mm diameter holes punched out in agar plates containing 0.2% AZCL galactan (Megazyme, Australia).

POLYNUCLEOTIDES:

Within preferred embodiments of the invention an isolated polynucleotide of the invention will hybridize to similar sized regions of SEQ ID No. 1, or a sequence complementary thereto, under at least medium stringency conditions.

In particular polynucleotides of the invention will hybridize to a denatured double-stranded DNA probe comprising either the full sequence shown in positions 1-1026 of SEQ ID NO:1 or any probe comprising a subsequence of SEQ ID NO:1 having a length of at least about 100 base pairs under at least medium stringency conditions, but preferably at high stringency conditions as described in detail below. Suitable experimental conditions for determining hybridization at medium, or high stringency between a nucleotide probe and a homologous DNA or RNA sequence involves presoaking of the filter containing the DNA fragments or RNA ta hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity higher than 1×10⁹ cpm/µg) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using a x-ray film.

As previously noted, the isolated polynucleotides of the present invention include DNA and RNA. Methods for isolating DNA and RNA are well known in the art. DNA and RNA encoding genes of interes can be cloned in Gene Banks or DNA libraries by means of methods known in the art.

Polynucleotides encoding polypeptides having pectate lyase activity of the invention are then identified and isolated by, for example, hybridization or PCR.

The present invention further provides counterpart polypeptides and polynucleotides from different bacterial strains (orthologs or paralogs). Of particular interest are pectate lyase polypeptides from gram-positive alkalophilic strains, including species of Bacillus.

Species homologues of a polypeptides pectate lyase activity of the invention can be cloned using information and compositions provided by the present invention in combination with conventional cloning techniques. For example, DNA can be cloned using chromosomal DNA obtained from a cell type that expresses the protein. Suitable sources of DNA can be identified by probing Northern blots with probes designed from the sequences disclosed herein. A library is then prepared from chromosomal DNA of a positive cell line. A DNA encoding an polypeptide having pectate lyase activity of the invention can then be isolated by a variety of methods, such as by probing with a complete or partial DNA or with one or more sets of degenerate probes based on the disclosed sequences. A DNA can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (mono-clonal or polyclonal) raised against the pectate lyase cloned from *B. licheniformis*, ATCC 14580, expressed and purified as described in Materials and Methods and Example 1, or by an activity test relating to a polypeptide having pectate lyase activity. Similar techniques can also be applied to the isolation of genomic clones.

The polypeptide encoding part of the DNA sequence cloned into plasmid pSJ1678 present in *Escherichia coli*

DSM 11789 and/or an analogue DNA sequence of the invention may be cloned from a strain of the bacterial species *Bacillus licheniformis*, preferably the strain ATCC 14580, producing the enzyme with pectin degrading activity, or another or related organism as described herein.

Alternatively, the analogous sequence may be constructed on the basis of the DNA sequence obtainable from the plasmid present in *Escherichia coli* DSM 11789, e.g be a sub-sequence thereof, and/or by introduction of nucleotide substitutions which do not give rise to another amino acid sequence of the pectat lyase encoded by the DNA sequence, but which corresponds to the codon usage of the host organism intended for production of the enzyme, or by introduction of nucleotide substitutions which may give rise to a different amino acid sequence (i.e. a variant of the pectin degrading enzyme of the invention).

POLYPEPTIDES:

The sequence of amino acids no. 1-341 of SEQ ID No 2 is a mature pectate lyase sequence.

The present invention also provides pectate lyase polypeptides that are substantially homologous to the polypeptides of SEQ ID NO:2 and their species homologs (paralogs or orthologs. The term "substantially homologous" is used herein to denote polypeptides having 80%, more preferably at least 85%, and even more preferably at least 90%, sequence identity to the sequence shown in SEQ ID NO:2 or their orthologs or paralogs. Such polypeptides will more preferably be at least 95% identical, and most preferably 98% or more identical to the sequence shown in SEQ ID NO:2 or its orthologs or paralogs. Percent sequence identity is determined by conventional methods, by means of computer programs known in the art such as GAP provided in the GCG program package (Program Manual for the Wisconsin Package, Version 8, August 1994, Genetics Computer Group, 575 Science Drive, Madison, Wis., USA 53711) as disclosed in Needleman, S. B. and Wunsch, C. D., (1970), Journal of Molecular Biology, 48, 443–453, which is hereby incorporated by reference in its entirety. GAP is used with the following settings for polypeptide sequence comparison: GAP creation penalty of 3.0 and GAP extension penalty of 0.1.

Sequence identity of polynucleotide molecules is determined by similar methods using GAP with the following settings for DNA sequence comparison: GAP creation penalty of 5.0 and GAP extension penalty of 0.3.

The enzyme preparation of the invention is preferably derived from a microorganism, preferably from a bacterium, an archea or a fungus, especially from a bacterium such as a bacterium belonging to Bacillus, preferably to an alkalophilic Bacillus strain which may be selected from the group consisting of the species *Bacillus licheniformis* and highly related Bacillus species in which all species preferably are at least 95%, even more preferably at least 98%, homologous to *Bacillus licheniformis* based on aligned 16S rDNA sequences.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions to a Pectate lyase polypeptide of the invention.

TABLE 1

Conservative amino acid substitutions

| | |
|---|---|
| Basic | arginine |
| | lysine |
| | histidine |
| Acidic | glutamic acid |
| | aspartic acid |
| Polar | glutamine |
| | asparagine |
| Hydrophobic | leucine |
| | isoleucine |
| | valine |
| Aromatic | phenylalanine |
| | tryptophan |
| | tyrosine |
| Small | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the pectate lyase polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (i.e pectate lyase activity) to identify amino acid residues that are critical to the activity of the molecule. See also, Hilton et al., *J. Biol. Chem.* 271:4699–4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science* 241:53–57, 1988), Bowie and Sauer (*Proc. Natl. Acad. Sci. USA* 86:2152–2156, 1989), WO95/17413, or WO95/22625. Briefly, these authors disclose methods for simultaneously randomizing two or more positions in a polypeptide, or recombination/shuffling of different mutations (WO95/17413, WO95/22625), followed by selecting for functional a polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 1 to 341 of SEQ ID NO: 2 and retain the pectate lyase activity of the wild-type protein.

The pectin degrading enzyme of the invention may, in addition to the enzyme core comprising the catalytically domain, also comprise a cellulose binding domain (CBD), the cellulose binding domain and enzyme core (the catalytically active domain) of the enzyme being operably linked. The cellulose binding domain (CBD) may exist as an integral part of the encoded enzyme, or a CBD from another origin may be introduced into the pectin degrading enzyme thus creating an enzyme hybrid. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I–X), and demonstrates that CBDs are found in various enzymes such as cellulases, xylanases, mannanases, arabinofuranosidases, acetyl esterases and chitinases. CBDs have also been found in algae, e.g. the red alga *Porphyra purpurea* as a non-hydrolytic polysaccharide-binding protein, see Tomme et al., op.cit. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the pectin degrading enzyme and growing the host cell to express the fused gene. Enzyme hybrids may be described by the following formula:

CBD–MR–X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to to about 100 amino acids, more preferably of from 2 to 40 amino acids; and X is an N-terminal or C-terminal region of the pectin degrading enzyme of the invention.

Preferably, the enzyme of the present invention has its maximum catalytic activity at a pH of at least 8, more preferably of at least 8.5, more preferably of at least 9, more preferably of at least 9.5, more preferably of at least 10, even more preferably of at least 10.5, especially of at least 11; and preferably the maximum activity of the enzyme is obtained at a temperature of at least 50° C., more preferably of at least 55° C.

PROTEIN PRODUCTION:

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Bacterial cells, particularly cultured cells of gram-positive organisms, are preferred. Gram-positive cells from the genus of Bacillus are especially preferred, such as *Bacillus subtilis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus thuringiensis, Bacillus agaradherens*, or in particular *Bacillus licheniformis*.

Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989; Ausubel et al. (eds.), *Current Protocols in Molecular Biology*, John Wiley and Sons, Inc., NY, 1987; and (*Bacillus subtilis* and Other Gram-Positive Bacteria, Sonensheim et al., 1993, American Society for Microbiology, Washington D.C.), which are incorporated herein by reference.

In general, a DNA sequence encoding a pectate lyase of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide into the secretory pathway of a host cell, a secretory signal sequence (also known as a leader sequence, prepro sequence or pre sequence) is provided in the expression vector. The secretory signal sequence may be that of the polypeptide, or may be derived from another secreted protein or synthesized de novo. Numerous suitable secretory signal sequences are known in the art and reference is made to (*Bacillus subtilis* and Other Gram-Positive Bacteria, Sonensheim et al., 1993, American Society for Microbiology, Washington D.C.; and Cutting, S. M.(eds.)

"Molecular Biological Methods for Bacillus". John Wiley and Sons, 1990) for further description of suitable secretory signal sequences especially for secretion in a Bacillus host cell. The secretory signal sequence is joined to the DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

PROTEIN ISOLATION:

When the expressed recombinant polypeptide is secreted the polypeptide may be purified from the growth media. Preferably the expression host cells are removed from the media before purification of the polypeptide (e.g. by centrifugation).

When the expressed recombinant polypeptide is not secreted from the host cell, the host cell are preferably disrupted and the polypeptide released into an aqueous "extract" which is the first stage of such purification techniques. Preferably the expression host cells are removed from the media before the cell disruption (e.g. by centrifugation).

The cell disruption may be performed by conventional techniques such as by lysozyme digestion or by forcing the cells through high pressure. See (Robert K. Scobes, Protein Purification, Second edition, Springer-Verlag) for further description of such cell disruption techniques.

Whether or not the expressed recombinant polypeptides (or chimeric polypeptides) is secreted or not it can be purified using fractionation and/or conventional purification methods and media.

Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers.

Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

Polypeptides of the invention or fragments thereof may also be prepared through chemical synthesis. Polypeptides of the invention may be monomers or multimers; glycosylated or non-glycosylated; pegylated or non-pegylated; and may or may not include an initial methionine amino acid residue.

Based on the sequence information disclosed herein a full length DNA sequence encoding a pectinase of the invention and comprising the DNA sequence shown in SEQ ID No 1 may be cloned.

Cloning of is performed by standard procedures known in the art such as by, preparing a genomic library from a Bacillus strain;
plating such a library on suitable substrate plates;
identifying a clone comprising a polynucleotide sequence of the invention by standard hybridization techniques using a probe based on SEQ ID No 1; or by
identifying a clone from said *Bacillus licheniformis* ATCC 14580 or DSM 8721 genomic library by an Inverse PCR strategy using primers based on sequence information from SEQ ID No 1. Reference is made to M. J. MCPherson et al. ("PCR A practical approach" Information Press Ltd, Oxford England) for further details relating to Inverse PCR.

Based on the sequence information disclosed herein (SEQ ID No 1, SEQ ID No 2) is it routine work for a person skilled in the art to isolate homologous polynucleotide sequences encoding homologous pectinase of the invention by a similar strategy using genomic libraries from related microbial organisms, in particular from genomic libraries from other strains of the genus Bacillus such as *Bacillus subtilis*.

Alternatively, the DNA encoding the pectin degrading enzyme of the invention may, in accordance with well-known procedures, conveniently be cloned from a suitable source, such as any of the below mentioned organisms, by use of synthetic oligonucleotide probes prepared on the basis of the DNA sequence obtainable from the plasmid present in *Escherichia coli* DSM 11789.

Accordingly, the polynucleotide molecule of the invention may be isolated from *Escherichia coli*, DSM 11789, in which the plasmid obtained by cloning such as described above is deposited. Also, the present invention relates to an isolated substantially pure biological culture of the strain *Escherichia coli*, DSM 11789.

In the present context, the term "enzyme preparation" is intended to mean either be a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species; or the fermentation product of a microorganism which acts as a host cell for expression of a recombinant pectate lyase, but which microorganism simultaneously produces other enzymes, e.g. pectin lyases, proteases, or cellulases, being naturally occurring fermentation products of the microorganism, i.e. the enzyme complex conventionally produced by the corresponding naturally occurring microorganism.

The pectate lyase preparation of the invention may further comprise one or more enzymes selected from the group consisting of proteases, cellulases (endo-β-1,4-glucanases), β-glucanases (endo-β-1,3(4)-glucanases), lipases, cutinases, peroxidases, laccases, amylases, glucoamylases, pectinases, reductases, oxidases, phenoloxidases, ligninases, pullulanases, arabinanases, hemicellulases, mannanases, xyloglucanases, xylanases, pectin acetyl esterases, rhamnogalacturonan acetyl esterases, polygalacturonases, rhamnogalacturonases, galactanases, pectin lyases, pectin methylesterases, cellobiohydrolases, transglutaminases; or mixtures thereof. In a preferred embodiment, one or more or all enzymes in the preparation is produced by using recombinant techniques, i.e. the enzyme(s) is/are monocomponent enzyme(s) which is/are mixed with the other enzyme(s) to form an enzyme preparation with the desired enzyme blend.

In another aspect, the present invention also relates to a method of producing the enzyme preparation of the invention, the method comprising culturing a microorganism capable of producing the pectate lyase under conditions permitting the production of the enzyme, and recovering the enzyme from the culture. Culturing may be carried out using conventional fermentation techniques, e.g. culturing in shake flasks or fermentors with agitation to ensure sufficient aeration on a growth medium inducing production of the pectate lyase enzyme. The growth medium may contain a conventional N-source such as peptone, yeast extract or casamino acids, a reduced amount of a conventional C-source such as dextrose or sucrose, and an inducer such as xyloglucan or composit plant substrates such as cereal brans (e.g. wheat bran or rice husk). The recovery may be carried out using conventional techniques, e.g. separation of biomass and supernatant by centrifugation or filtration, recovery of the supernatant or disruption of cells if the enzyme of interest is intracellular, perhaps followed by further purification as described in EP 0 406 314 or by crystallization as described in WO 97/15660.

IMMUNOLOGICAL CROSS-REACTIVITY:

Polyclonal antibodies to be used in determining immunological cross-reactivity may be prepared by use of a purified pectate lyase enzyme. More specifically, antiserum against the pectate lyase of the invention may be raised by immunizing rabbits (or other rodents) according to the procedure described by N. Axelsen et al. in: A Manual of Quantitative Immunuoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation (($NH_4$)$_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Examples of useful bacteria producing the enzyme or the enzyme preparation of the invention are Gram positive bacteria, preferably from the Bacillus/Lactobacillus subdivision, preferably a strain from the genus Bacillus, especially a strain of *Bacillus licheniformis*. ATCC 14580 is the type strain of *Bacillus licheniformis*.

In yet another aspect, the present invention relates to an isolated pectate lyase having the properties described above and which is free from homologous impurities, and is produced using conventional recombinant techniques.

Use in the Detergent Industry

In further aspects, the present invention relates to a detergent composition comprising the pectate lyase or pectate lyase preparation of the invention, and to a process for machine treatment of fabrics comprising treating fabric during a washing cycle of a machine washing process with a washing solution containing the pectate lyase or pectate lyase preparation of the invention.

Typically, the detergent composition of the invention comprises conventional ingredients such as surfactants (anionic, nonionic, zwitterionic, amphoteric), builders, and other ingredients, e.g. as described in WO 97/01629 which is hereby incorporated by reference in its entirety.

Use in the Textile and Cellulosic Fiber Processing Industries

The pectate lyase of the present invention can be used in combination with other carbohydrate degrading enzymes (for instance arabinanase, xyloglucanase, pectinase) for biopreparation of fibers or for cleaning of fibers in combination with detergents. Cotton fibers consist of a primary cell wall layer containing pectin and a secondary layer containing mainly cellulose. Under cotton preparation or cotton refining part of the primary cell wall will be removed. The present invention relates to either help during cotton refining by removal of the primary cell wall. Or during cleaning of the cotton to remove residual pectic substances and prevent graying of the textile.

In the present context, the term "cellulosic material" is intended to mean fibers, sewn and unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, hemp, flax/linen, jute, cellulose acetate fibers, lyocell).

The preparation of the present invention is useful in the cellulosic fiber processing industry for the pretreatment or retting of fibers from hemp, flax or linen.

The processing of cellulosic material for the textile industry, as for example cotton fiber, into a material ready for garment manufacture involves several steps: spinning of the fiber into a yarn; construction of woven or knit fabric from the yarn and subsequent preparation, dyeing and finishing operations. Woven goods are constructed by weaving a filling yarn between a series of warp yarns; the yarns could be two different types. Knitted goods are constructed by forming a network of interlocking loops from one continuous length of yarn. The cellulosic fibers can also be used for non-woven fabric.

The preparation process prepares the textile for the proper response in dyeing operations. The sub-steps involved in preparation are a. Desizing (for woven goods) using polymeric size like e.g. starch, CMC or PVA is added before weaving in order to increase the warp speed; This material must be removed before further processing.
b. Scouring, the aim of which is to remove non-cellulosic material from the cotton fiber, especially the cuticle (mainly consisting of waxes) and primary cell wall (mainly consisting of pectin, protein and xyloglucan). A proper wax removal is necessary for obtaining a high wettability, being a measure for obtaining a good dyeing. Removal of the primary cell wall—especially the pectins—improves wax removal and ensures a more even dyeing. Further this improves the whiteness in the bleaching process. The main chemical used in scouring is sodium hydroxide in high concentrations, up to 70 g/kg cotton and at high temperatures, 80–95° C.; and
c. Bleaching; normally the scouring is followed by a bleach using hydrogen peroxide as the oxidizing agent in order to obtain either a fully bleached (white) fabric or to ensure a clean shade of the dye.

A one step combined scour/bleach process is also used by the industry. Although preparation processes are most commonly employed in the fabric state; scouring, bleaching and dyeing operations can also be done at the fiber or yarn stage.

The processing regime can be either batch or continuous with the fabric being contacted by the liquid processing stream in open width or rope form. Continuous operations generally use a saturator whereby an approximate equal weight of chemical bath per-weight of fabric is applied to the fabric, followed by a heated dwell chamber where the chemical reaction takes place. A washing section then prepares the fabric for the next processing step. Batch processing generally takes place in one processing bath whereby the fabric is contacted with approximately 8–15 times its weight in chemical bath. After a reaction period, the chemicals are drained, fabric rinsed and the next chemical is applied. Discontinuous pad-batch processing involves a saturator whereby an approximate equal weight of chemical bath per weight of fabric is applied to the fabric, followed by a dwell period which in the case of cold pad-batch might be one or more days.

Woven goods are the prevalent form of textile fabric construction. The weaving process demands a "sizing" of the warp yarn to protect it from abrasion. Starch, polyvinyl alcohol (PVA), carboxymethyl cellulose, waxes and acrylic binders are examples of typical sizing chemicals used because of availability and cost. The size must be removed after the weaving process as the first step in preparing the woven goods. The sized fabric in either rope or open width form is brought in contact with the processing liquid containing the desizing agents. The desizing agent employed depends upon the type of size to be removed. For PVA sizes, hot water or oxidative processes are often used. The most common sizing agent for cotton fabric is based upon starch. Therefore most often, woven cotton fabrics are desized by a combination of hot water, the enzyme a-amylase to hydrolyze the starch and a wetting agent or surfactant. The cellulosic material is allowed to stand with the desizing chemicals for a "holding period" sufficiently long to accomplish the desizing. The holding period is dependent upon the type of processing regime and the temperature and can vary from 15 minutes to 2 hours, or in some cases, several days. Typically, the desizing chemicals are applied in a saturator bath which generally ranges from about 15° C. to about 55° C. The fabric is then held in equipment such as a "J-box" which provides sufficient heat, usually between about 55° C. and about 100° C., to enhance the activity of the desizing agents. The chemicals, including the removed sizing agents, are washed away from the fabric after the termination of the holding period.

In order to ensure a high whiteness or a good wettability and resulting dyeability, the size chemicals and other applied chemicals must be thoroughly removed. It is generally believed that an efficient desizing is of crucial importance to the following preparation processes: scouring and bleaching.

The scouring process removes much of the non-cellulosic compounds naturally found in cotton. In addition to the natural non-cellulosic impurities, scouring can remove dirt, soils and residual manufacturing introduced materials such as spinning, coning or slashing lubricants. The scouring process employs sodium hydroxide or related causticizing agents such as sodium carbonate, potassium hydroxide or mixtures thereof. Generally an alkali stable surfactant is added to the process to enhance solubilization of hydrophobic compounds and/or prevent their redeposition back on the fabric. The treatment is generally at a high temperature, 80° C.–100° C., employing strongly alkaline solutions, pH 13–14, of the scouring agent. Due to the non-specific nature of chemical processes not only are the impurities but the cellulose itself is attacked, leading to damages in strength or other desirable fabric properties. The softness of the cellulosic fabric is a function of residual natural cotton waxes. The non-specific nature of the high temperature strongly alkaline scouring process cannot discriminate between the desirable natural cotton lubricants and the manufacturing introduced lubricants. Furthermore, the conventional scouring process can cause environmental problems due to the highly alkaline effluent from these processes. The scouring stage prepares the fabric for the optimal response in bleaching. An inadequately scoured fabric will need a higher level of bleach chemical in the subsequent bleaching stages.

The bleaching step decolorizes the natural cotton pigments and removes any residual natural woody cotton trash components not completely removed during ginning, carding or scouring. The main process in use today is an alkaline hydrogen peroxide bleach. In many cases, especially when a very high whiteness is not needed, bleaching can be combined with scouring.

In the examples below it is shown that the scouring step can be carried out using the pectate lyase or pectate lyase preparation of the present invention a temperature of about 50° C. 80° C. and a pH of about 7–11, thus substituting or supplementing the highly causticizing agents. An optimized enzymatic process ensures a high pectin removal and full wettability.

Degradation or Modification of Plant Material

The enzyme or enzyme preparation according to the invention is preferably used as an agent for degradation or modification of plant cell walls or any pectin-containing material originating from plant cells walls due to the high plant cell wall degrading activity of the pectate lyase of the invention.

The pectate lyase of the present invention may be used alone or together with other enzymes like glucanases, pectinases and/or hemicellulases to improve the extraction of oil from oil-rich plant material, like soy-bean oil from soybeans, olive-oil from olives or rapeseed-oil from rape-seed or sunflower oil from sunflower.

The pectate lyase of the present invention may be used for separation of components of plant cell materials. Of particular interest is the separation of sugar or starch rich plant material into components of considerable commercial interest (like sucrose from sugar beet or starch from potato) and components of low interest (like pulp or hull fractions). Also, of particular interest is the separation of protein-rich or oil-rich crops into valuable protein and oil and invaluable hull fractions, The separation process may be performed by use of methods known in the art.

The pectate lyase of the invention may also be used in the preparation of fruit or vegetable juice in order to increase yield, and in the enzymatic hydrolysis of various plant cell wall-derived materials or waste materials, e.g. from wine or juice production, or agricultural residues such as vegetable hulls, bean hulls, sugar beet pulp, olive pulp, potato pulp, and the like.

The plant material may be degraded in order to improve different kinds of processing, facilitate purification or extraction of other component than the galactans like purification of pectins from citrus, improve the feed value, decrease the water binding capacity, improve the degradability in waste water plants, improve the conversion of plant material to ensilage, etc.

By means of an enzyme preparation of the invention it is possible to regulate the consistency and appearence of processed fruit or vegetables. The consistency and appearence has been shown to be a product of the actual combination of enzymes used for processing, i.e. the specificity of the enzymes with which the pectate lyase of the invention is combined. Examples include the production of clear juice e.g. from-apples, pears or berries; cloud stable juice e.g. from apples, pears, berries, citrus or tomatoes; and purees e.g. from carrots and tomatoes.

The pectate lyase of the invention may be used in modifying the viscosity of plant cell wall derived material. For instance, the pectate lyase may be used to reduce the viscosity of feed which contain galactan and to promote processing of viscous galactan containing material. The viscosity reduction may be obtained by treating the galactan containing plant material with an enyme preparation of the invention under suitable conditions for full or partial degradation of the galactan containing material The pectate lyase can be used e.g. in combination with other enzymes for the removal of pectic substances from plant fibres. This removal is essential e.g. in the production of textile fibres or other cellulosic materials. For this purpose plant fibre material is treated with a suitable amount of the pectate lyase of the invention under suitable conditions for obtaining full or partial degradation of pectic substances associated with the plant fibre material.

Animal Feed Additive

Pectate lyases of the present invention may be used for modification of animal feed and may exert their effect either in vitro (by modifying components of the feed) or in vivo. The pectate lyase is particularly suited for addition to animal feed compositions containing high amounts of arabinogalactans or galactans, e.g. feed containing plant material from soy bean, rape seed, lupin etc. When added to the feed the pectate lyase significantly improves the in vivo break-down of plant cell wall material, whereby a better utilization of the plant nutrients by the animal is achieved. Thereby, the growth rate and/or feed conversion ratio (i.e. the weight of ingested feed relative to weight gain) of the animal is improved. For example the indigestible galactan is degraded by pectate lyase, e.g. in combination with $\beta$-galactosidase, to galactose or galactooligomers which are digestible by the animal and thus contribute to the available energy of the feed. Also, by the degradation of galactan the pectate lyase may improve the digestibility and uptake of non-carbohydrate feed constituents such as protein, fat and minerals.

For further description reference is made to PCT/DK 96/00443 and a working example herein.

Wine and Juice Processing

The enzyme or enzyme preparation of the invention may be used for de-pectinization and viscosity reduction in vegetable or fruit juice, especially in apple or pear juice. This may be accomplished by treating the fruit or vegetable juice with an enzyme preparation of the invention in an amount effective for degrading pectin-containing material contained in the fruit or vegetable juice.

The enzyme or enzyme preparation may be used in the treatment of mash from fruits and vegetables in order to improve the extractability or degradability of the mash. For instance, the enzyme preparation may be used in the treatment of mash from apples and pears for juice production, and in the mash treatment of grapes for wine production.

DETERMINATION OF CATALYTIC ACTIVITY OF PECTATE LYASE

The Viscosity Assay APSU

APSU units: The APSU unit assay is a viscosity measurement using the substrate polygalacturonic acid with no added calcium.

The substrate 5% polygalacturonic acid sodium salt (Sigma P-1879) is solubilised in 0.1 M Glycin buffer pH 10. The 4 ml substrate is preincubated for 5 min at 40° C. The enzyme is added (in a volume of 250 $\mu$l) and mixed for 10 sec on a mixer at maximum speed, it is then incubated for 20 min at 40° C. For a standard curve double determination of a dilution of enzyme concentration in the range of 5 APSU/ml to above 100 APSU/ml with minimum of 4 concentrations between 10 and 60 APSU per ml The viscosity is measured using a MIVI 600 from the company Sofraser, 45700 Villemandeur, France. The viscosity is measured as mV after 10 sec.

For calculation of APSU units a enzyme standard dilution as described above was used for obtaining a standard curve. The GrafPad Prism program, using a non linear fit with a one phase exponential decay with a plateau, was used for calculations. The plateau plus span is the mV obtained without enzyme. The plateau is the mV of more than 100 APSU and the half reduction of viscosity in both examples was found to be 12 APSU units with a standard error of 1.5 APSU.

The Lyase Assay (at 235 nm)

For determination of the $\beta$-elimination an assay measuring the increase in absorbance at 235 nm was carried out using the substrate 0.1% polygalacturonic acid sodium salt (Sigma P-1879) solubilised in 0.1 M Glycin buffer pH 10. For calculation of the catalytic rate an increase of 5.2 Absorbency at 235 units per min corresponds to formation of 1 $\mu$mol of unsaturated product (Nasuna and Starr (1966) J. Biol. Chem. Vol 241 page 5298–5306; and Bartling, Wegener and Olsen (1995) Microbiology Vol 141 page 873–881).

Steady state condition using a 0.5 ml cuvette with a 1 cm light path on a HP diode array spectrophotometer in a temperature controlled cuvette holder with continuous measurement of the absorbency at 235 nm. For steady state a linear increase for at least 200 sec was used for calculation of the rate. It was used for converted to formation pmol per min product.

MATERIALS AND METHODS

Strains

*Bacillus licheniformis* ATCC 14580.

*B. subtilis* PL2306. This strain is the *B. subtilis* DN1885 with disrupted apr and npr genes (Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol., 172, 4315–4321) disrupted in the transcriptional unit of the known *Bacillus subtilis* cellulase gene, resulting in cellulase negative cells. The disruption was performed essentially as described in (Eds. A. L. Sonenshein, J. A. Hoch and Richard Losick (1993) *Bacillus subtilis* and other Gram-Positive Bacteria, American Society for microbiology, p.618).

Competent cells were prepared and transformed as described by Yasbin, R. E., Wilson, G. A. and Young, F. E. (1975) Transformation and transfection in lysogenic strains of *Bacillus subtilis*: evidence for selective induction of prophage in competent cells. J. Bacteriol, 121:296–304.
Plasmids
pMOL944:

This plasmid is a pUB110 derivative essentially containing elements making the plasmid propagatable in *Bacillus subtilis*, kanamycin resistance gene and having a strong promoter and signal peptide cloned from the amyL gene of *B. licheniformis* ATCC14580. The signal peptide contains a SacII site making it convenient to clone the DNA encoding the mature part of a protein in-fusion with the signal peptide. This results in the expression of a Pre-protein which is directed towards the exterior of the cell.

The plasmid was constructed by means of conventional genetic engineering techniques which are briefly described in the following.
Construction of pMOL944:

The pUB110 plasmid (McKenzie, T. et al., 1986, Plasmid 15:93–103) was digested with the unique restriction enzyme NciI. A PCR fragment amplified from the amyl promoter encoded on the plasmid pDN1981 (P. L. Jørgensen et al., 1990, Gene, 96, p37–41.) was digested with NciI and inserted in the NciI digested pUB110 to give the plasmid pSJ2624.
The two PCR primers used have the following sequences:
LWN5494
5'-GTCGCCGGGGCGGCCGCTATCAATTGGTAA CTGTATCTCAGC-3' (SEQ ID NO:3)
LWN5495
5'-GTCGCCCGGGAGCTCTGATCAGGTACCAAG CTTGTCGACCTGCAGAA TGAGGCAGCAAGAAGAT-3' (SEQ ID NO:4).

The primer #LWN5494 inserts a NotI site in the plasmid.

The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670.

This cloning replaces the first amyL promoter cloning with the same promoter but in the opposite direction. The two primers used for PCR amplification have the following sequences:
LWN5938
5'-GTCGGCGGCCGCTGATCACGTACCAAGCTTG TCGACCTGCAGAATG AGGCAGCAAGAAGAT-3' (SEQ ID NO:5)
LWN5939
5'-GTCGGAGCTCTATCAATTGGTAACTGTATCTC AGC-3' (SEQ ID NO:6)

The plasmid pSJ2670 was digested with the restriction enzymes PstI and BclI and a PCR fragment amplified from a cloned DNA sequence encoding the alkaline amylase SP722 (disclosed in the International Patent Application published as WO95/26397 which is hereby incorporated by reference in its entirety) was digested with PstI and BclI and inserted to give the plasmid pMOL944. The two primers used for PCR amplification have the following sequence:
LWN7864
5'-AACAGCTGATCACGACTGATCTTTTAGCTTG GCAC-3' (SEQ ID NO:7)
LWN7901
5'-AACTGCAGCCGCGGCACATCATAATGGGAC AAATGGG-3' (SEQ ID NO:8)
The primer #LWN7901 inserts a SacII site in the plasmid.

Genomic DNA Preparation

Strain *Bacillus licheniformis* ATCC 14580 was propagated in liquid medium 3 as specified by ATCC (American Type Culture Collection, USA). After 18 hours incubation at 37° C. and 300 rpm, the cells were harvested, and genomic DNA isolated by the method described by Pitcher et al. (Pitcher, D. G., Saunders, N. A., Owen, R. J. (1989). Rapid extraction of bacterial genomic DNA with guanidium thiocyanate. Lett. Appl. Microbiol., 8, 151–156).

The pectate lyase encoding DNA sequence of the invention was PCR amplified using the PCR primer set consisting of these two oligo nucleotides:
Pecl.B.lich.upper.SacII 5'-CTA ACT GCA GCC GCG GCA GCT TCT GCC TTA AAC TCG GGC-3' (SEQ ID NO:9)
Pecl.B.lich.lower.NotI 5'-GCG TTG AGA CGC GCG GCC GCT GAA TGC CCC GGA CGT TTC ACC-3' (SEQ ID NO:10)
Restriction sites SacII and NotII are underlined.

Chromosomal DNA isolated from *B.licheniformis* ATCC 14580 as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM $MgCl_2$, 0.01% (w/v) gelatin) containing 200 µM of each dNTP, 2.5 units of AmpliTaq polymerase (Perkin-Elmer, Cetus, USA) and 100 pmol of each primer.

The PCR reactions was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-µl aliquots of the amplification product was analysed by electrophoresis in 0.7% agarose gels (NuSieve, FMC). The appearance of a DNA fragment size 1.0 kb indicated proper amplification of the gene segment.
Subcloning of PCR Fragment.

Fortyfive-µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5. 5 µg of pMOL944 and twentyfive-µl of the purified PCR fragment was digested with SacII and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 µg of each DNA fragment, 1 U of T4 DNA ligase and T4 ligase buffer (Boehringer Mannheim, Germany).

The ligation mixture was used to transform competent *B. subtilis* PL2306. The transformed cells were plated onto LBPG-10 µg/ml of Kanamycin plates. After 18 hours incubation at 37° C. several clones were restreaked on fresh agar plates and also grown in liquid TY cultures with 10 µg/ml kanamycin and incubated overnight at 37° C. Next day 1 ml of cells were used to isolate plasmid from the cells using the Qiaprep Spin Plasmid Miniprep Kit #27106 according to the manufacturers recommendations for *B. subtilis* plasmid preparations. This plasmid DNA was used as template for DNA sequencing.

One clone containing the pectate lyase gene was kept, this clone was termed MB541.

The DNA corresponding to the mature part of the pectate lyase was characterised by DNA sequencing by primerwalking, using the Taq deoxy-terminal cycle sequencing kit (Perkin-Elmer, USA), fluorescent labelled terminators and appropriate oligonucleotides as primers.

Analysis of the sequence data was performed according to Devereux et al. (1984) Nucleic Acids Res. 12, 387–395. The cloned DNA sequence was expressed in *B.subtilis* and the protein that appeared in the supernatant corresponded to the mature protein represented in SEQ ID NO:2.

Media

TY. (as described in Ausubel, F. M. et al. (eds.) "Current protocols in Molecular Biology". John Wiley and Sons, 1995).

LB agar (as described in Ausubel, F. M. et al. (eds.) "Current protocols in Molecular Biology". John Wiley and Sons, 1995).

LBPG is LB agar supplemented with 0.5% Glucose and 0.05 M potassium phosphate, pH 7.0

BPX media is described in EP 0 506 780 (WO 91/09129).

The following examples illustrate the invention.

EXAMPLE 1

Purification and Characterization of Pectate Lyase from *Bacillus licheniformis*

MB541 (see Materials and Methods) was grown in 25×200 ml BPX media with 10 µg/ml of Hanamycin in 500 ml two baffled shakeflasks for 5 days at 37° C. at 300 rpm, whereby 3500 ml of culture broth was obtained. The pH was adjusted to 5.0 using acetic acid and 100 ml of cationic agent (C521) and 200 ml of anionic agent (A130) was added during agitation for flocculation. The flocculated material was separated by centrifugation using a Sorval RC 3B centrifuge at 10000 rpm for min at 6° C. The resulting supernatant contained 370 APSU per ml in a total volume of 3600 ml.

The supernatant was clarified using Whatman glass filters GF/D and C and finally concentrated on a filtron with a cut off of 10 kDa. The total volume of 2000 ml was adjusted to pH 8.5. 50 gram of DEAE A-50 Sephadex (Pharmacia) was swelled in 2000 ml 50 mM Tris pH 8.5. Excess buffer was discarded and the clear concentrated enzyme solution was mixed with the slurry for 15 min. The enzyme was separated from the ion-exchange material by suction on a Buchner funnel. The resulting solution was concentrated on a filtron with a cut off of 10 kDa.

The solution (700 ml) was formulated using 350 gram of sorbitol giving a product MB 541–2 batch 9751.

For obtaining a highly purified pectate lyase a final step using S-sepharose cation-exchange chromatography was carried out. 50 ml of the solution of 950 APSU per ml (see above) was adjusted to pH 5.0 using acetic acid. It was applied to a 50 ml column containing S-Sepharose (Pharmacia) equilibrated with a buffer of 50 mmol sodium acetate pH 5.0.

The pectate lyase bound and was eluted using a gradient of 0.5 M sodium chloride. The pure enzyme gave a single band in SDS-PAGE of 35 kDa and has a pI of 9.3. The protein concentration was determined using a molar extinction coefficient of 57750 (based on the amino acid composition deducted from the sequence). Using the assay of detection the formation of cleavage by the formation of a double bound which can be measured at 235 nm the following data were obtained 1. (conditions: pH 10; glycine buffer; no calcium; polygalacturonic acid Sigma P-1879 as substrate): 1 µmol per min per mg.
2. (conditions: pH 10; glycine buffer; no calcium; DE 35 (35% esterified pectin) as substrate): 4 µmol per min per mg.

The temperature optimum was found to be 65° C.

Rabbit antiserum was raised against the purified pectate lyase using standard conditions (0.1 mg protein per rabbit per immunization).

EXAMPLE 2

Pectate Lyase Treatment of Cellulosic Material

Effect of Temperature on Pectin Removal and Wettability

A 100% cotton woven twill fabric, desized Test Fabric #428U, representing a typical cellulosic material, was treated with an aqueous enzyme solution comprising the *B. licheniformis* pectate lyase of this invention, dosed at 9 APSU/g fabric at pH 9 and at a 15:1 liquor ratio. Treatment time was 2 hours and temperature varied between 35–75° C. The fabric was rinsed well after the enzyme treatment, dried and then dyed with Ruthenium Red. The dye uptake was measured spectrophotometrically and is a measure of the residual pectin on the fiber. The percentage of residual pectin was calculated using the dye uptake of the starting material as 100% residual pectin and that of fully chemically scoured and bleached fabric as 0%. Results are shown in Table 1. Further, the wettability (drop test—measuring the time in seconds for a drop of water to become absorbed by the fabric) was measured and compared to a no enzyme control. Results are shown in Table 2.

TABLE 1

| | (% residual pectin) | | | | |
| --- | --- | --- | --- | --- | --- |
| Temp., ° C. | 35 | 45 | 55 | 65 | 75 |
| no enzyme | 100 | 100 | 93 | 90 | 85 |
| enzyme | 52 | 40 | 32 | 28 | 26 | an alkaline scouring leaves typically 20–25% residual pectin

TABLE 2

| Temp., ° C. | 35 | 45 | 55 | 65 | 75 |
| --- | --- | --- | --- | --- | --- |
| no enzyme | 32 | 29 | 29 | 12 | 11 |
| enzyme | 15 | 10 | 7 | 5 | 3 | wettability target is typically <5 seconds

The beneficial effect of increasing temperature is clearly seen on both responses.

EXAMPLE 3

Pectate Lyase Treatment of Cellulosic Material
Effect of pH on Pectin Removal

A 100% cotton woven twill fabric, desized Test Fabric #428U, representing a typical cellulosic material, was treated with an aqueous enzyme solution comprising the *B. licheniformis* pectate lyase of the invention, dosed at 9 APSU/g fabric at a 15:1 liquor ratio. Treatment time was 2 hours and the temperature 55° C. pH was varied between 8–11. The fabric was rinsed well after the enzyme treatment, dried and then dyed with Ruthenium Red. The dye uptake is measured spectrophotometrically and is a measure of the residual pectin on the fiber. The percentage of residual pectin was calculated using the dye uptake of the starting material as 100% residual pectin and that of fully chemically scoured and bleached fabric as 0%. The results are shown in Table 3:

TABLE 3

| pH | 8 | 9 | 10 | 10.5 | 11 |
|---|---|---|---|---|---|
| % residual pectin | 35 | 32 | 30 | 48 | 61 |

The pH optimum is found to be at app. 9.5, but a good activity is demonstrated in a very broad alkaline interval.

EXAMPLE 4

Use of the Enzyme of the Invention in Detergents

The purified enzyme obtained as described in example 1 (batch 9751) showed improved cleaning performance when tested at a level of 1 ppm in a miniwash test using a conventional commercial liquid detergent. The test was carried out under conventional North American wash conditions.

LITERATURE

Lever, M. (1972) A new reaction for colormetric determination of carbohydrates. Anal. Biochem. 47, 273–279.

N. C. Carpita and D. M. Gibeaut (1993) The Plant Journal 3:1–30.

Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol. 172:4315–4321.

---

What is claimed is:

1. An isolated polynucleotide molecule encoding a polypeptide having pectate lyase activity selected from the group consisting of:
   a) polynucleotide molecules comprising a nucleotide sequence as shown in SEQ ID NO: 1 from nucleotide 1 to nucleotide 1026;
   b) polynucleotide molecules that encode a polypeptide having at least 95% identity to the amino acid sequence of SEQ ID NO: 2 from amino acid residue 1 to amino acid residue 341, wherein said identity is determined by the GAP program, using a GAP creation peialty of 3.0 and a GAP extension penalty of 0.1; and
   c) polynucleotide molecules encoding a pectate lyase, wherein said polynucleotide molecules hybridize to the DNA sequence of SEQ ID NO: 1 under high stringency conditions, wherein said high stringency conditions comprise hybridization in 5×SSC at 45° C. and washing in 2×SSC at 70° C.

2. The isolated polynucleotide molecule according to claim 1, wherein the polynucleotide is DNA.

3. An expression vector comprising the following operably linked elements: a transcription promoter; a DNA segment encoding a polypeptide having pectate lyase activity as defined in claim 2; and a transcription terminator.

4. A cultured cell into which has been introduced an expression vector according to claim 3, wherein said cell expresses the polypeptide encoded by the DNA segment.

5. A method of producing a polypeptide having pectate lyase activity, said method comprising:
   (a) culturing a cell into which has been introduced an expression vector according to claim 3, under conditions suitable for expression of a polypeptide encoded by the DNA segment; and
   (b) recovering the polypeptide.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1026 base pairs
      (B) TYPE: nucleic acid
      (C) STRANDEDNESS: single
      (D) TOPOLOGY: linear (xi) SEQUENCE DESCRIPTION: SEQ ID NO:1:

```
ATGAAGAAAT TAATCAGCAT CATCTTTATC TTTGTATTAG GGGTTGTCGG GTCATTGACA      60

GCGGCGGTTT CGGCAGAAGC AGCTTCTGCC TTAAACTCGG GCAAAGTAAA TCCGCTTGCC     120

GACTTCAGCT TAAAAGGCTT TGCCGCACTA AACGGCGGAA CAACGGGCGG AGAAGGCGGT     180

CAGACGGTAA CCGTAACAAC GGGAGATCAG CTGATTGCGG CATTAAAAAA TAAGAATGCA     240

AATACGCCTT TAAAAATTTA TGTCAACGGC ACCATTACAA CATCAAATAC ATCCGCATCA     300

AAGATTGACG TCAAAGACGT GTCAAACGTA TCGATTGTCG GATCAGGGAC CAAAGGGGAA     360

CTCAAAGGGA TCGGCATCAA AATATGGCGG GCCAACAACA TCATCATCCG CAACTTGAAA     420

ATTCACGAGG TCGCCTCAGG CGATAAAGAC GCGATCGGCA TTGAAGGCCC TTCTAAAAAC     480

ATTTGGGTTG ATCATAATGA GCTTTACCAC AGCCTGAACG TTGACAAAGA TTACTATGAC     540

GGATTATTTG ACGTCAAAAG AGATGCGAAA TATATTCACA TCTCTTGGAA CTATGTGCAC     600

GATGGATGGA AATCAATGCT GATGGGTTCA TCGGACAGCG ATAATTACAA CAGGACGATT     660

ACATTCCATC ATAACTGGTT TGAGAATCTG AATTCGCGTG TGCCGTCATT CCGTTTCGGA     720

GAAGGCCATA TTTACAACAA CTATTTCAAT AAAATCATCG ACAGCGGAAT TAATTCGAGG     780

ATGGGCGCGC GCATCAGAAT TGAGAACAAC CTCTTTGAAA ACGCCAAAGA TCCGATTGTC     840
```

```
TCTTGGTACA GCAGTTCACC GGGCTATTGG CATGTATCCA ACAACAAATT TGTAAACTCT     900

AGGGGCAGTA TGCCGACTAC CTCTACTACA ACCTATAATC CGCCATACAG CTACTCACTC     960

GACAATGTCG ACAATGTAAA ATCAATCGTC AAGCAAAATG CCGGAGTCGG CAAAATCAAT    1020

CCATAA                                                                1026
```

(2) INFORMATION FOR SEQ ID NO:2:

(i) SEQUENCE CHARACTERISTICS:
        (A) LENGTH: 341 amino acids
        (B) TYPE: amino acid
        (C) STRANDEDNESS: single
        (D) TOPOLOGY: linear (xi) SEQUENCE DESCRIPTION: SEQ ID NO:2:

```
Met Lys Lys Leu Ile Ser Ile Ile Phe Ile Phe Val Leu Gly Val Val
 1               5                  10                  15

Gly Ser Leu Thr Ala Ala Val Ser Ala Glu Ala Ala Ser Ala Leu Asn
            20                  25                  30

Ser Gly Lys Val Asn Pro Leu Ala Asp Phe Ser Leu Lys Gly Phe Ala
        35                  40                  45

Ala Leu Asn Gly Gly Thr Thr Gly Gly Glu Gly Gln Thr Val Thr
50                  55                  60

Val Thr Thr Gly Asp Gln Leu Ile Ala Ala Leu Lys Asn Lys Asn Ala
65                  70                  75                  80

Asn Thr Pro Leu Lys Ile Tyr Val Asn Gly Thr Ile Thr Thr Ser Asn
                85                  90                  95

Thr Ser Ala Ser Lys Ile Asp Val Lys Asp Val Ser Asn Val Ser Ile
            100                 105                 110

Val Gly Ser Gly Thr Lys Gly Glu Leu Lys Gly Ile Gly Ile Lys Ile
        115                 120                 125

Trp Arg Ala Asn Asn Ile Ile Ile Arg Asn Leu Lys Ile His Glu Val
130                 135                 140

Ala Ser Gly Asp Lys Asp Ala Ile Gly Ile Glu Gly Pro Ser Lys Asn
145                 150                 155                 160

Ile Trp Val Asp His Asn Glu Leu Tyr His Ser Leu Asn Val Asp Lys
                165                 170                 175

Asp Tyr Tyr Asp Gly Leu Phe Asp Val Lys Arg Asp Ala Glu Tyr Ile
            180                 185                 190

Thr Phe Ser Trp Asn Tyr Val His Asp Gly Trp Lys Ser Met Leu Met
        195                 200                 205

Gly Ser Ser Asp Ser Asp Asn Tyr Asn Arg Thr Ile Thr Phe His His
210                 215                 220

Asn Trp Phe Glu Asn Leu Asn Ser Arg Val Pro Ser Phe Arg Phe Gly
225                 230                 235                 240

Glu Gly His Ile Tyr Asn Asn Tyr Phe Asn Lys Ile Ile Asp Ser Gly
                245                 250                 255

Ile Asn Ser Arg Met Gly Ala Arg Ile Arg Ile Glu Asn Asn Leu Phe
            260                 265                 270

Glu Asn Ala Lys Asp Pro Ile Val Ser Trp Tyr Ser Ser Ser Pro Gly
        275                 280                 285

Tyr Trp His Val Ser Asn Asn Lys Phe Val Asn Ser Arg Gly Ser Met
290                 295                 300

Pro Thr Thr Ser Thr Thr Thr Tyr Asn Pro Pro Tyr Ser Tyr Ser Leu
305                 310                 315                 320
```

```
Asp Asn Val Asp Asn Val Lys Ser Ile Val Lys Gln Asn Ala Gly Val
            325                 330                 335
Gly Lys Ile Asn Pro
        340
```

(2) INFORMATION FOR SEQ ID NO:3:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:3:

```
GTCGCCGGGG CGGCCGCTAT CAATTGGTAA CTGTATCTCA GC                        42
```

(2) INFORMATION FOR SEQ ID NO:4:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:4:

```
GTCGCCCGGG AGCTCTGATC AGGTACCAAG CTTGTCGACC TGCAGAATGA GGCAGCAAGA     60

AGAT                                                                 64
```

(2) INFORMATION FOR SEQ ID NO:5:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:5:

```
GTCGGCGGCC GCTGATCACG TACCAAGCTT GTCGACCTGC AGAATGAGGC AGCAAGAAGA     60

T                                                                    61
```

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:6:

```
GTCGGAGCTC TATCAATTGG TAACTGTATC TCAGC                               35
```

(2) INFORMATION FOR SEQ ID NO:7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:7:

```
AACAGCTGAT CACGACTGAT CTTTTAGCTT GGCAC                               35
```

(2) INFORMATION FOR SEQ ID NO:8:

(i) SEQUENCE CHARACTERISTICS:

```
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:8:

AACTGCAGCC GCGGCACATC ATAATGGGAC AAATGGG                                37

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:9:

CTAACTGCAG CCGCGGCAGC TTCTGCCTTA AACTCGGGC                              39

(2) INFORMATION FOR SEQ ID NO:10:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GCGTTGAGAC GCGCGGCCGC TGAATGCCCC GGACGTTTCA CC                          42
```